United States Patent
Akhatou et al.

(10) Patent No.: US 11,891,375 B2
(45) Date of Patent: Feb. 6, 2024

(54) METHOD FOR THE SYNTHESIS OF 2,4-DIMETHYLPYRIMIDIN-5-OL, INTERMEDIATES, AND METHOD FOR THE SYNTHESIS OF LEMBOREXANT USING THE INTERMEDIATES

(71) Applicant: MOEHS IBERICA, S.L., Barcelona (ES)

(72) Inventors: Abdeslam Akhatou, Lessines (BE); Alicia Dobarro Rodríguez, Barcelona (ES)

(73) Assignee: MOEHS IBERICA, S.L., Barcelona (ES)

( * ) Notice: Subject to any disclaimer, the term of this patent is extended or adjusted under 35 U.S.C. 154(b) by 0 days.

(21) Appl. No.: 17/814,815

(22) Filed: Jul. 25, 2022

(65) Prior Publication Data
US 2023/0092143 A1    Mar. 23, 2023

(30) Foreign Application Priority Data
Jul. 26, 2021   (ES) .................. ES202130723

(51) Int. Cl.
*C07D 401/12* (2006.01)
*C07C 201/14* (2006.01)
*C07D 239/34* (2006.01)
*C07D 239/36* (2006.01)

(52) U.S. Cl.
CPC .......... *C07D 401/12* (2013.01); *C07C 201/14* (2013.01); *C07D 239/34* (2013.01); *C07D 239/36* (2013.01); *C07B 2200/13* (2013.01)

(58) Field of Classification Search
CPC .. C07D 401/12; C07D 239/34; C07D 239/36; C07C 201/14
See application file for complete search history.

(56) References Cited

U.S. PATENT DOCUMENTS
2008/0064871 A1   3/2008  Hirata et al.

FOREIGN PATENT DOCUMENTS
EP    2814798          12/2014
EP    3178814 A1       6/2017
WO    WO 2013/123240 A1   8/2013

OTHER PUBLICATIONS

Search Report issued in ES Application No. 202130723, dated Jun. 20, 2022.

*Primary Examiner* — Deepak R Rao
(74) *Attorney, Agent, or Firm* — Knobbe, Martens, Olson & Bear, LLP

(57) ABSTRACT

A method is for the synthesis of 2,4-dimethylpyrimidin-5-ol, which can be used as an intermediate compound in the synthesis of Lemborexant. The method includes reacting a nitrophenyl compound with N,N-dimethylformamide diethyl acetal.

19 Claims, 4 Drawing Sheets

METHOD FOR THE SYNTHESIS OF 2,4-DIMETHYLPYRIMIDIN-5-OL, INTERMEDIATES, AND METHOD FOR THE SYNTHESIS OF LEMBOREXANT USING THE INTERMEDIATES

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

The present invention relates to a novel method for the synthesis of 2,4-dimethylpyrimidin-5-ol, which is a useful intermediate in the synthesis of Lemborexant, to novel intermediates of said method, and to the use of the products in the synthesis of Lemborexant.

Description of the Related Art

Lemborexant is a medicinal product for the treatment of insomnia characterized by difficulty falling asleep or staying asleep.

Lemborexant or (1S,2R)-2-[(2,4-dimethylpyrimidin-5-yl)oxymethyl]-2-(3-fluorophenyl)-N-(5-fluoro-2-pyridinyl)cyclopropanecarboxamide has the following chemical structure:

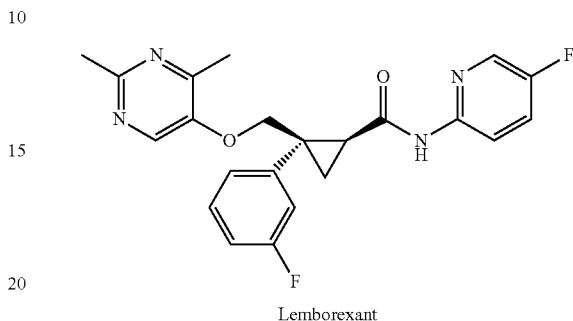

Lemborexant

European patent EP3178814B1 describes a method for obtaining Lemborexant comprising the following steps:

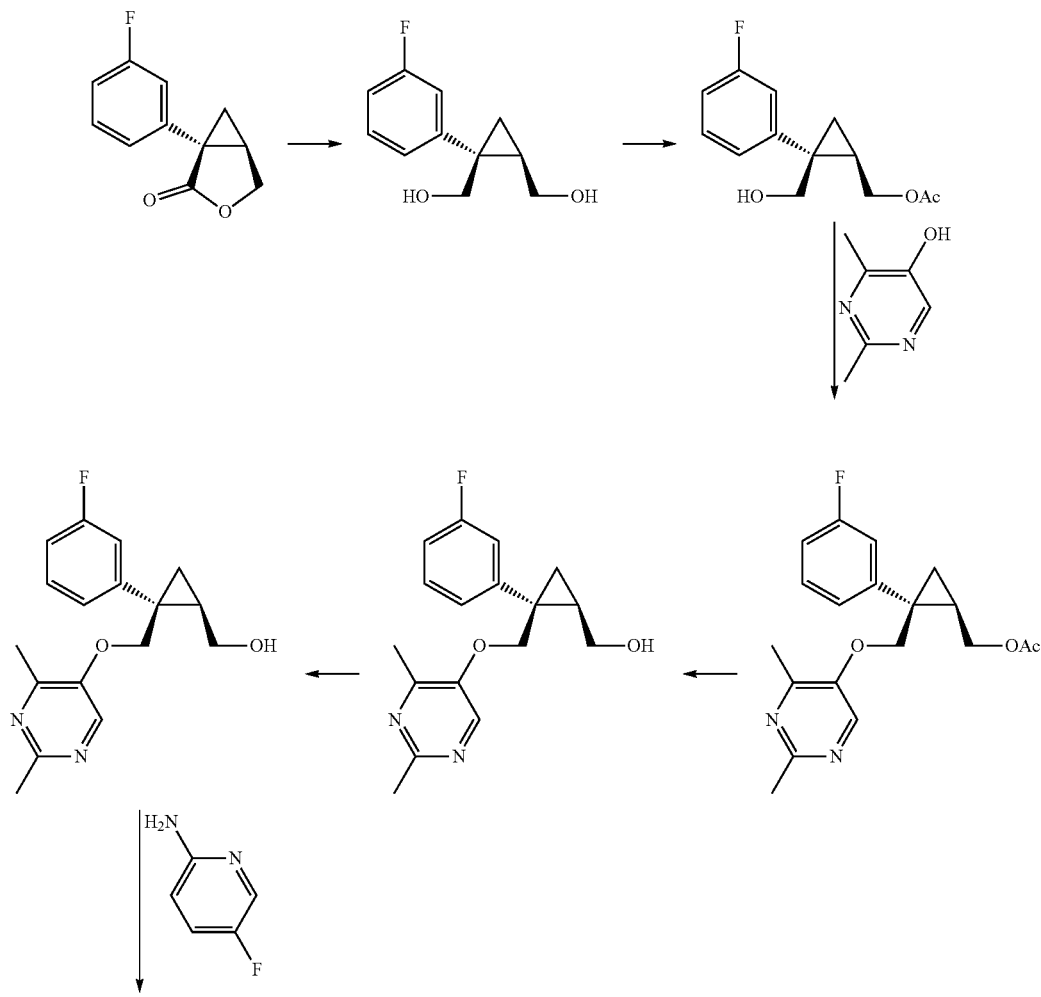

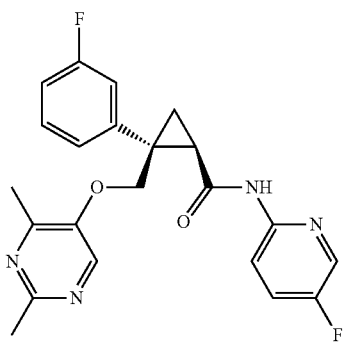

As can be observed in the synthetic scheme above, the compound, 2,4-dimethylpyrimidin-5-ol, the structure of which is shown below

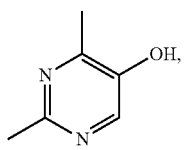

is a key intermediate for the production of Lemborexant.

European patent EP3178814B1 refers to documents WO 2012/039371 and WO2013/123240, which describe methods for obtaining the compound 2,4-dimethylpyrimidin-5-ol. Furthermore, European patent EP3178814B1 itself describes another method for obtaining said intermediate.

The method described in document WO 2012/039371 comprises the following steps:

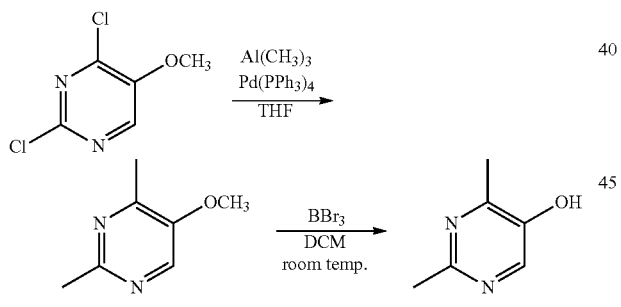

The method described in document WO 2013/123240 comprises the following steps:

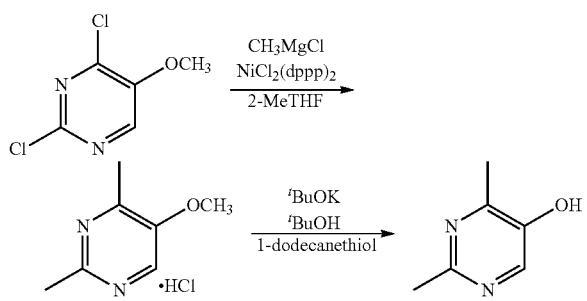

The methods described in documents WO 2012/039371 and WO 2013/123240 are not suitable for the industrial manufacture of 2,4-dimethylpyrimidin-5-ol since they use, as the starting material, 2,4-dichloro-5-methoxypyrimidine, which is an expensive product, they involve the intermediate, 2,4-dimethyl-5-methoxypyrimidine, which is a volatile product, or its hydrochloride which is a hygroscopic product, as well as corrosive irritant reagents which require working under extreme precaution, such as trimethylaluminum or boron tribromide, for example.

Therefore, European patent EP3178814B1 develops a method for the synthesis of the industrially applicable intermediate, 2,4-dimethylpyrimidin-5-ol, solving the aforementioned problems.

The synthesis described in document EP3178814B1 comprises the following steps:

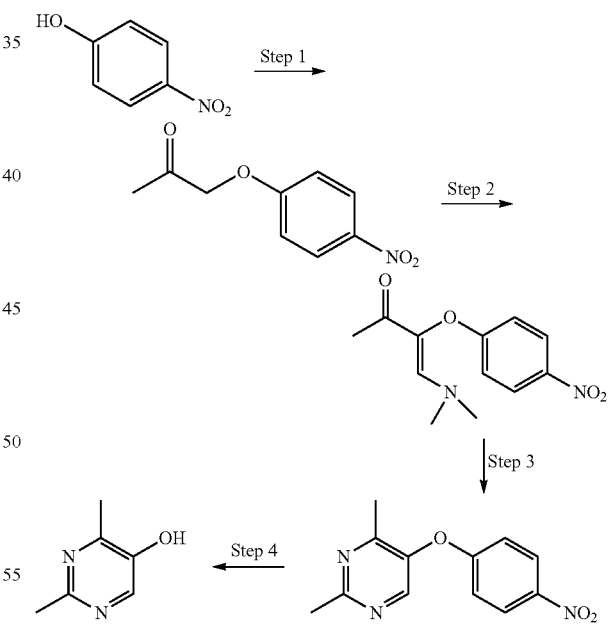

In this synthesis, the readily available compound 4-nitrophenol is used as the starting material, and N,N-dimethylformamide dimethyl acetal is used in step 2 of the method. Furthermore, the 4-nitrophenyl group helps in the regioselective condensation of step 3, and furthermore serves as a protecting group that can be separated under relatively mild conditions in hydrolysis step 4.

Despite the improvements described in EP3178814B1 for obtaining the key intermediate 2,4-dimethylpyrimidin-5-ol at the industrial level, there is a need to provide even further optimized methods, particularly with a higher yield, for the synthesis of said intermediate of the product Lemborexant on an industrial scale.

SUMMARY OF THE INVENTION

The inventors have surprisingly discovered that the yield unexpectedly increases by using N,N-dimethylformamide diethyl acetal instead of N,N-dimethylformamide dimethyl acetal in step 2 of the preparation of 2,4-dimethylpyrimidin-5-ol (key intermediate in the synthesis of Lemborexant) described in EP3178814B1. As described in EP3178814B1, the yield of this step would range between 41% and 55%, whereas in the present invention, yields of about 65% are achieved by using N,N-dimethylformamide diethyl acetal. Furthermore, the yield improves even further by substituting p-nitrophenol of EP3178814B1 with o-nitrophenol, reaching about 85%. Furthermore, both the key intermediate 2,4-dimethylpyrimidin-5-ol and intermediates of the method of synthesis thereof are obtained with high levels of purity.

Therefore, in a first aspect, the present invention relates to a method for preparing a compound of formula (I) or a stereoisomer or salt thereof

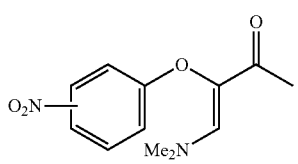
(I)

which comprises reacting a compound of formula (II) with N,N-dimethylformamide diethyl acetal

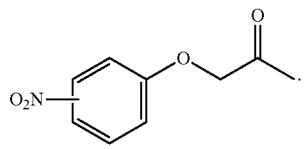
(II)

In a second aspect, the present invention relates to a method for preparing the compound of formula (III) or a salt thereof

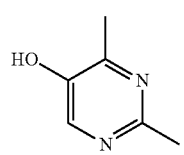
(III)

which comprises:
performing the method defined in the first aspect in order to obtain the compound of formula (I) or a stereoisomer or salt thereof

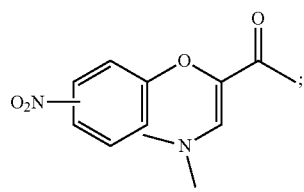
(I)

and transforming the compound of formula (I) or a stereoisomer or salt thereof into a compound of formula (III) or a salt thereof.

In particular, the method defined in said aspect comprises:
a) performing the method defined in the first aspect in order to obtain the compound of formula (I) or a stereoisomer or salt thereof

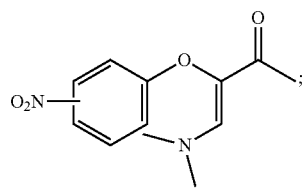
(I)

b) reacting the compound of formula (I) or a stereoisomer or salt thereof with the compound of formula (IV) or a salt thereof in the presence of a base in order to yield the compound of formula (V) or a salt thereof

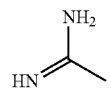
(IV)

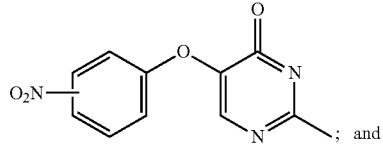
(V)

; and and
c) hydrolyzing the compound of formula (V) or a salt thereof in order to yield the compound of formula (III) or a salt thereof.

In a third aspect, the invention relates to a method for preparing Lemborexant which comprises:
a) performing the method defined in the second aspect in order to obtain the compound of formula (III) or a salt thereof

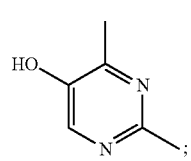
(III)

b) reacting the compound of formula (III) or a salt thereof with a compound of formula (VIII) in the presence of a base in order to yield a compound of formula (IX)

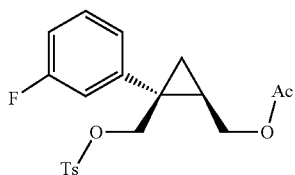

(VIII)

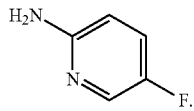

(XII)

In a fourth aspect, the invention relates to a crystalline form of the compound of formula (IIa)

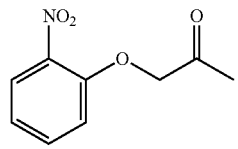

(IIa)

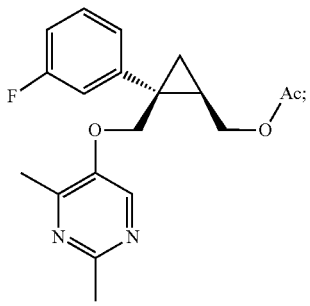

(IX)

characterized in that it has an X-ray powder diffraction spectrum measured with CuKα radiation comprising peaks at 9.9, 12.2, 16.2, 18.7, 20.0, 24.5, 27.0 °2θ±0.2 °2θ.

In a fifth aspect, the invention relates to a compound of formula (Ia) or a stereoisomer or salt thereof

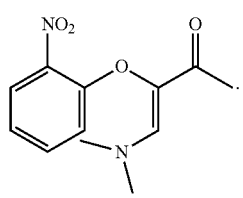

(Ia)

c) hydrolyzing the compound of formula (IX) in the presence of a base in order to yield a compound of formula (X)

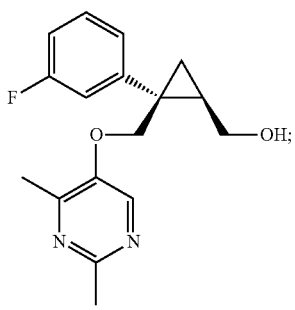

(X)

In a sixth aspect, the invention relates to a compound of formula (Va)

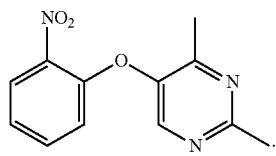

(Va)

d) treating the compound of formula (X) with an oxidizing agent in order to yield a compound of formula (XI)

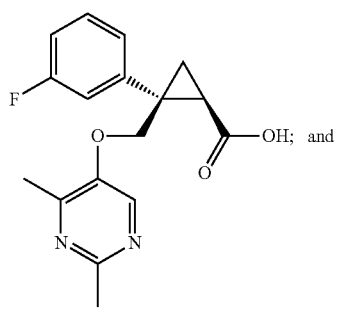

(XI)

In another aspect, the invention relates to the use of the compound of formula (IIa), of the compound of formula (Ia) or a stereoisomer or salt thereof, of the compound of formula (Va), and/or of the crystalline forms of said compounds in the preparation of the compound of formula (III) or a salt thereof.

In another aspect, the invention relates to the use of the compound of formula (IIa), of the compound of formula (Ia) or a stereoisomer thereof, of the compound of formula (Va), and/or of the crystalline forms of said compounds in the preparation of Lemborexant.

In another aspect, the invention relates to a crystalline form of the compound of formula (III), characterized in that the X-ray powder diffraction spectrum thereof measured with CuKα radiation comprises peaks at 12.8, 15.5, 16.6, 17.9, 21.8, 22.1, 23.6, 25.0, 25.7, 27.1, 30.1 °2θ±0.2 °2θ.

BRIEF DESCRIPTION OF THE DRAWINGS

and e) reacting the compound of formula (XI) with a compound of formula (XII) in the presence of a base and a coupling agent in order to yield Lemborexant

DETAILED DESCRIPTION OF THE PREFERRED EMBODIMENT

Figure 1:
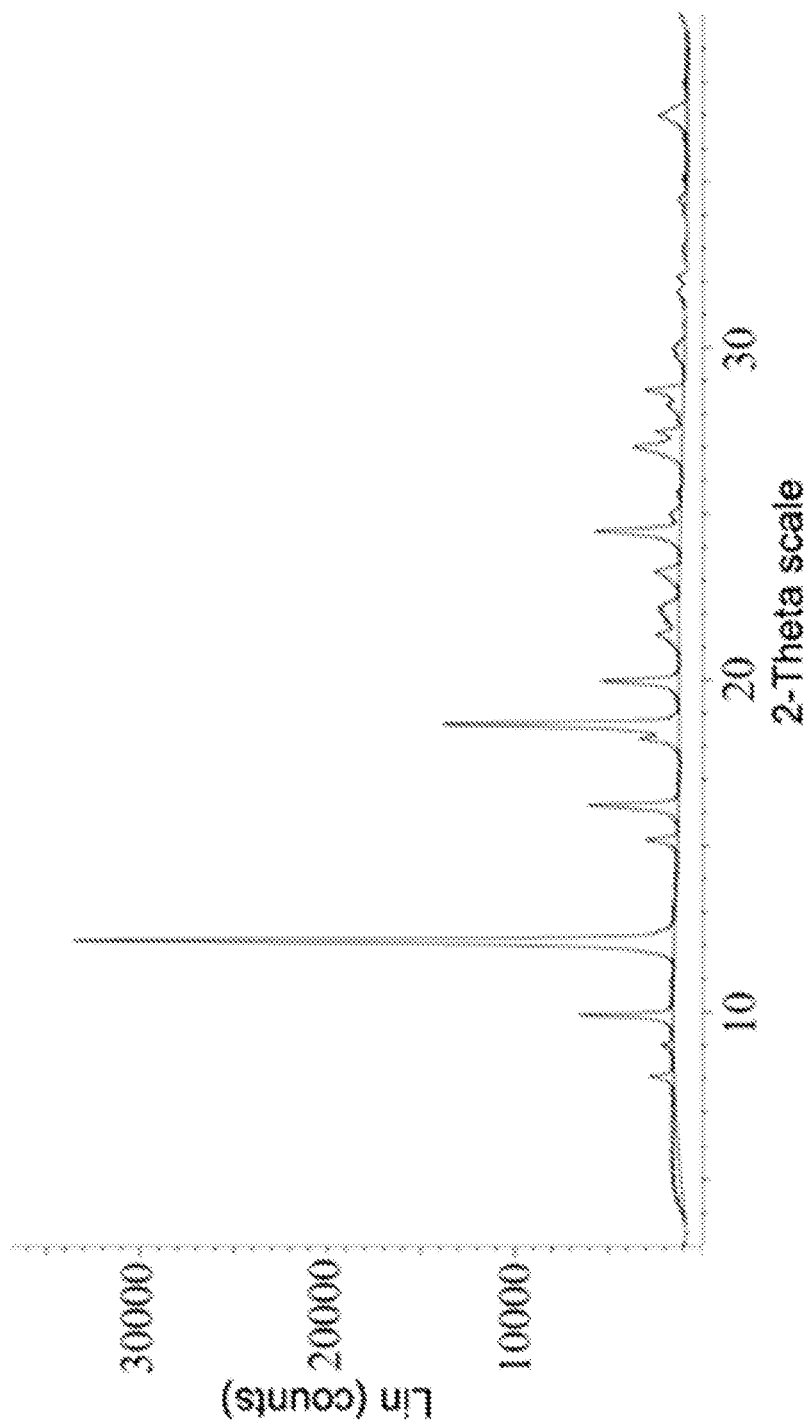
FIG. 1 shows the X-ray powder diffractogram (XRPD) of the compound of formula (IIa) corresponding to 1-(2-nitrophenoxy)propan-2-one.

Method for Preparing the Compound of Formula (I)

The first aspect of the present invention relates to a method for preparing a compound of formula (I) or a stereoisomer or salt thereof

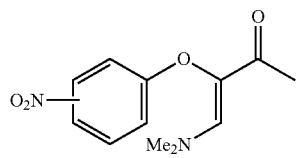

(I)

which comprises reacting a compound of formula (II) with N,N-dimethylformamide diethyl acetal

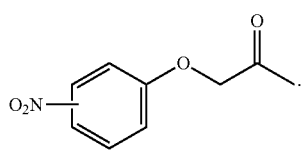

(II)

Said method is similar to that described in EP3178814B1, but using N,N-dimethylformamide diethyl acetal instead of N,N-dimethylformamide dimethyl acetal. Surprisingly, this reagent substitution provides a method with a higher reaction yield. As described in EP3178814B1, the yield of this step would range between 41% and 55%, whereas in the present invention, yields of at least about 65% are achieved by using N,N-dimethylformamide diethyl acetal.

The —$NO_2$ group (nitro group) of the compound of formula (I) can be in an ortho, meta, or para position (with respect to another phenyl ring substituent), preferably in an ortho or para position, more preferably in an ortho position.

When the —$NO_2$ group of the compound of formula (I) is in an ortho position, the —$NO_2$ group in the compound of formula (II) is also in an ortho position. When the —$NO_2$ group of the compound of formula (I) is in a para position, the —$NO_2$ group in the compound of formula (II) is also in a para position. When the —$NO_2$ group of the compound of formula (I) is in a meta position, the —$NO_2$ group in the compound of formula (II) is also in a meta position.

Compounds of formula (I) and (II) with the —$NO_2$ group in a para position are described in EP3178814B1.

The inventors have observed that when the —$NO_2$ group is in an ortho position, the reaction yield is higher. Therefore, in a preferred embodiment, the —$NO_2$ group is in an ortho position.

In a preferred embodiment, the proportion of N,N-dimethylformamide diethyl acetal with respect to the compound of formula (II) is from 1 to 2 moles of N,N-dimethylformamide diethyl acetal for every mole of the compound of formula (II), more preferably from 1.05 to 2, more preferably from 1.05 to 1.3.

The reaction can be carried out both in the presence of solvent and in the absence of solvent.

In one embodiment, the reaction is carried out in the presence of solvent. When it is performed in the presence of solvent, the solvent is preferably an aromatic hydrocarbon such as, for example, toluene or xylene, more preferably toluene.

In another embodiment, the reaction is carried out in the absence of solvent.

The method can preferably be carried out at temperatures of between 35° C. and 90° C., more preferably between 35° C. and 60° C., even more preferably between 35° C. and 50° C., even more preferably between 45° C. and 50° C.

The reaction is preferably carried out at least 3 hours, preferably at least 4 h, more preferably up to a maximum of 24 hours. In a particular embodiment, the reaction is carried out from 3 to 6 hours.

The reaction is carried out keeping the reaction mixture under stirring.

In a preferred embodiment, after the reaction a next step of adding a protic or aprotic polar solvent such as, for example, $C_1$-$C_4$ alkanol type solvents or $C_1$-$C_4$ dialkyl ethers, to the obtained reaction mixture is carried out. Examples of these solvents would be isopropanol, tert-butanol, methyl-tert-butyl ether, or diisopropyl ether. Preferably, 2 to 6 mL of solvent would be added for every gram of compound of formula (II), preferably 3 to 5 mL of solvent for every gram of compound of formula (II). The solvent used is preferably diisopropyl ether. In particular, this treatment comprises adding diisopropyl ether to the obtained reaction mixture. Preferably, after adding the solvent, the resulting mixture is cooled at a temperature of 20° C. to 25° C., preferably with stirring, more preferably for 10 to 15 hours. Preferably, after this time has elapsed, the mixture is cooled at a temperature of 0 to 5° C., preferably with stirring. This treatment yields a suspension and the resulting solid (compound of formula (I)) can be separated by conventional means such as by means of filtration, for example. Treatment with diisopropyl ether has the advantage of purifying the compound of formula (I).

Stereoisomers of the compound of formula (I) refer to the position of the substituents with respect to the double bond, where they can be in a cis (Z) or trans (E) position.

The compound of formula (I) refers both to the cis isomer and to the trans isomer and any mixture thereof, preferably the cis isomer.

It must be understood that the term "salt" means any form of the defined compounds that are in an ionic form or charged and coupled with a counterion (a cation or anion), or in dissolution. For example, salts of the compounds of formula (I) can be acid addition salts and can be synthesized from the original compound containing a basic moiety by means of conventional chemical methods. Generally, such salts are prepared, for example, by reacting the free base forms of those compounds with a stoichiometric amount of suitable acid in water or in an organic solvent or in a mixture of both. Generally, non-aqueous media such as ether, ethyl acetate, ethanol, isopropanol, or acetonitrile are preferred. Examples of acid addition salts include mineral acid addition salts such as, for example, hydrochloride, hydrobromide, hydroiodide, sulfate, nitrate, phosphate, and organic acid addition salts such as, for example, acetate, maleate, fumarate, citrate, oxalate, succinate, tartrate, malate, mandelate, methanesulfonate, and p-toluenesulfonate.

Method for Preparing the Compound of Formula (III)

In a second aspect, the present invention relates to a method for preparing the compound of formula (III) or a salt thereof, which is a key intermediate in the synthesis of Lemborexant

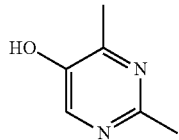
(III)

which comprises:
performing the method defined in the first aspect in order to obtain the compound of formula (I) or a stereoisomer or salt thereof

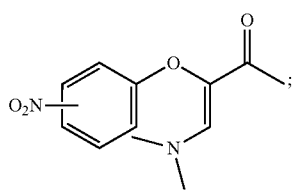
(I)

and transforming the compound of formula (I) or a stereoisomer or salt thereof into a compound of formula (III) or a salt thereof.

Transformation of the compound of formula (I) or a stereoisomer or salt thereof into a compound of formula (III) or a salt thereof can be carried out using any method of synthesis known to one skilled in the art.

Preferably, said method comprises:
a) performing the method defined in the first aspect in order to obtain the compound of formula (I) or a stereoisomer or salt thereof

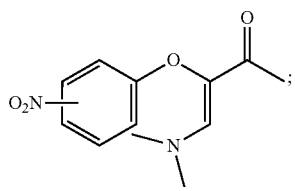
(I)

b) reacting the compound of formula (I) or a stereoisomer or salt thereof with the compound of formula (IV) or a salt thereof in the presence of a base in order to yield the compound of formula (V) or a salt thereof

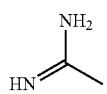
(IV)

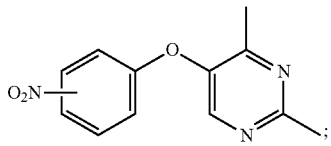
(V)

c) hydrolyzing the compound of formula (V) or a salt thereof in order to yield the compound of formula (III) or a salt thereof.

The first step of the method of the second aspect is to carry out the method of the first aspect of the invention, described in detail above.

The —NO$_2$ group (nitro group) of the compound of formula (I) can be in an ortho, meta, or para position (with respect to another phenyl ring substituent), preferably in an ortho or para position, more preferably in an ortho position.

When the —NO$_2$ group of the compound of formula (I) is in an ortho position, the —NO$_2$ group in the compound of formula (V) is also in an ortho position. When the —NO$_2$ group of the compound of formula (I) is in a para position, the —NO$_2$ group in the compound of formula (V) is also in a para position. When the —NO$_2$ group of the compound of formula (I) is in a meta position, the —NO$_2$ group in the compound of formula (V) is also in a meta position.

Compounds of formula (I) and (V) with the —NO$_2$ group in a para position are described in EP3178814B1.

The inventors have observed that when the —NO$_2$ group is in an ortho position, the reaction yield is greater. Therefore, in a preferred embodiment, the —NO$_2$ group is in an ortho position.

Step b) of the method of the second aspect comprises reacting the compound of formula (I) or a stereoisomer or salt thereof with the compound of formula (IV) or a salt thereof in the presence of a base in order to yield the compound of formula (V) or a salt thereof

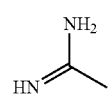
(IV)

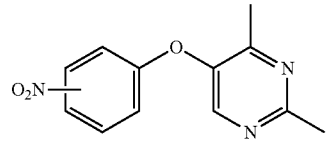
(V)

The term "salt" must be understood to mean any form of the defined compounds which are in an ionic form or charged and coupled with a counterion (a cation or anion), or in dissolution. For example, salts of the compounds of formula (I), of formula (IV), and of formula (V) can be acid addition salts and can be synthesized from the original compound containing a basic moiety by means of conventional chemical methods. Generally, such salts are prepared, for example, by reacting the free base forms of those compounds with a stoichiometric amount of suitable acid in water or in an organic solvent or in a mixture of both. Generally, non-aqueous media such as ether, ethyl acetate, ethanol, isopropanol, or acetonitrile are preferred. Examples of acid addition salts include mineral acid addition salts such as, for example, hydrochloride, hydrobromide, hydroiodide, sulfate, nitrate, phosphate, and organic acid addition salts such as, for example, acetate, maleate, fumarate, citrate, oxalate, succinate, tartrate, malate, mandelate, methanesulfonate, and p-toluenesulfonate.

In a particular embodiment, the compound of formula (IV) is in the form of hydrochloride salt.

Step b) of the method is performed in the presence of a base. In the context of the present invention, the term "base" refers to a substance capable of accepting a proton (of an acid). Examples of bases suitable for step b) are alkali metal $C_1$-$C_4$ alkoxides, preferably sodium $C_1$-$C_4$ alkoxide, more preferably sodium ethoxide or sodium methoxide, even more preferably sodium ethoxide.

The expression "alkali metal" refers to a metal selected from sodium, potassium, lithium, rubidium, cesium, and francium, preferably sodium or potassium, more preferably sodium.

The term "alkoxide" refers to an alkyl-$O^-$ group, wherein "alkyl" is a linear or branched hydrocarbon chain radical consisting of carbon and hydrogen atoms, not containing unsaturations, and having the indicated number of carbon atoms (for example, from 1 to 4 carbon atoms, preferably 1 to 3, more preferably 1 or 2, and attached to $O^-$ by means of a single bond). Examples of alkoxides are methoxide, ethoxide, n-propoxide, isopropoxide, tert-butoxide, n-butoxide, preferably methoxide or ethoxide, more preferably ethoxide.

In particular, 1 to 4 moles of base are used in step b) for every mole of the compound of formula (IV) or a salt thereof, preferably 2 to 3, more preferably 2.4 to 2.6.

Step b) is preferably performed in the presence of a solvent selected from the group consisting of $C_1$-$C_4$ alkanol, preferably ethanol, methanol, or a mixture thereof, even more preferably ethanol.

The term "alkanol" refers to an alkyl-OH group, wherein alkyl is as defined above. Examples of $C_1$-$C_4$ alkanols are methanol, ethanol, n-propanol, isopropanol, n-butanol, tert-butanol, sec-butanol, iso-butanol, preferably methanol and ethanol.

Preferably, in step b), the alkyl group of the alkanol and alkoxide is the same. More preferably, step b) is performed using sodium ethoxide as a base and ethanol as a solvent or sodium methoxide as a base and methanol as a solvent, even more preferably, step b) is performed using sodium ethoxide as a base and ethanol as a solvent.

In a particular embodiment, 1 to 3 moles of the compound of formula (IV) or a salt thereof are used in step b) for every mole of the compound of formula (I) or a stereoisomer or salt thereof, preferably 1 to 4, more preferably 2 to 3, even more preferably 2.2 to 2.6.

In particular, step b) is performed at a temperature of 50° C. to 80° C., preferably 65° C. to 80 C. Step b) is preferably performed from 3 to 10 h. It is preferably performed with stirring.

The compound of formula (V) of step b) is preferably not in the form of salt, i.e., is in a free base form.

The next step of the method of the second aspect is step c) of hydrolyzing the compound of formula (V) or a salt thereof in order to yield the compound of formula (III) or a salt thereof.

As explained above, it must be understood that the term "salt" means any form of the defined compounds which are in an ionic form or charged and coupled with a counterion (a cation or anion), or in dissolution. For example, salts of the compound of formula (III) can be base addition salts and can be synthesized from the original compound containing an acid moiety by means of conventional chemical methods.

Generally, such salts are prepared, for example, by reacting the free acid forms of those compounds with a stoichiometric amount of the suitable base in water or in an organic solvent or in a mixture of both. Generally, non-aqueous media such as ether, ethyl acetate, ethanol, isopropanol, or acetonitrile are preferred. Examples of base addition salts include inorganic salts such as, for example, ammonium, and organic alkaline salts such as, for example, ethylenediamine, ethanolamine, N,N-dialkylenethanolamine, triethanolamine, glucamine, and basic amino acid salts. Examples of metal salts include, for example, sodium, potassium, calcium, magnesium, aluminum, and lithium salts.

In a preferred embodiment, step c) is performed in the presence of a base selected from the group consisting of alkali metal hydroxide, alkali metal carbonate, and alkaline earth metal carbonate. Examples of bases are sodium hydroxide, potassium hydroxide, potassium carbonate, sodium carbonate, cesium carbonate, calcium carbonate, and magnesium carbonate.

The expression "alkaline earth metal" refers to a metal selected from the group consisting of beryllium, magnesium, calcium, strontium, barium, and radium, preferably magnesium and calcium.

In a preferred embodiment, the base of step c) is an alkali metal hydroxide, preferably sodium hydroxide or potassium carbonate, more preferably sodium hydroxide.

In particular, 1 to 5 moles of base are used in step c) for every mole of the compound of formula (V) or a salt thereof, preferably 2 to 4, more preferably 2.5 to 3.5.

In a preferred embodiment, step c) is performed in the presence of an aqueous solvent, preferably a mixture of water and $C_1$-$C_4$ alkanol, preferably a mixture of water and ethanol or a mixture of water and methanol, even more preferably a mixture of water and ethanol.

In particular, step c) is performed at a temperature of 50° C. to 80° C., preferably 60° C. to 70 C. Step c) is preferably performed from 15 to 24 h. It is preferably performed with stirring.

The compound of formula (III) obtained in step c) can be isolated from the reaction medium by means of conventional techniques.

In particular embodiments of the methods of the first and second aspects of the invention, the compound of formula (II) is obtained by means of reacting a compound of formula (VI) and a compound of formula (VII), wherein X is chlorine or bromine, preferably chlorine.

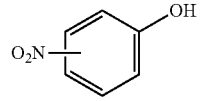

(VI)

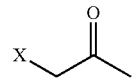

(VII)

The —$NO_2$ group (nitro group) of the compound of formula (VI) can be in an ortho, meta, or para position (with respect to another phenyl ring substituent), preferably in an ortho or para position, more preferably in an ortho position.

When the —$NO_2$ group of the compound of formula (VI) is in an ortho position, the —$NO_2$ group in the compound of formula (II) is also in an ortho position. When the —$NO_2$ group of the compound of formula (VI) is in a para position, the —$NO_2$ group in the compound of formula (II) is also in a para position. When the —NO$_2$ group of the compound of formula (VI) is in a meta position, the —NO$_2$ group in the compound of formula (II) is also in a meta position.

The inventors have observed that when the —NO$_2$ group is in an ortho position, the reaction yield is greater. Therefore, in a preferred embodiment, the —NO$_2$ group is in an ortho position.

In a particular embodiment, 1 to 2 moles of the compound of formula (VI) are used for every mole of the compound of formula (VII), preferably 1 to 1.5 moles, more preferably 1 to 1.1 moles.

In a preferred embodiment, the reaction of the compound of formula (VI) and the compound of formula (VII) is performed in the presence of a base and a phase-transfer catalyst.

The base is preferably an alkali metal or alkaline earth metal carbonate. Examples of bases are potassium carbonate, sodium carbonate, cesium carbonate, calcium carbonate, and magnesium carbonate, preferably potassium carbonate. In a particular embodiment, 1 to 2 moles of base are used for every mole of the compound of formula (VI), preferably 1 to 1.5 moles, more preferably 1 to 1.1 moles.

Examples of phase-transfer catalysts are quaternary ammonium salts such as, for example, tetrabutylammonium iodide and tetramethylammonium iodide. The phase-transfer catalyst is preferably tetrabutylammonium iodide (TBAI). In a particular embodiment, 0.001 to 0.1 g of phase-transfer catalyst is used for every gram of the compound of formula (VI), preferably 0.001 to 0.01.

In a preferred embodiment, the base is an alkali metal or alkaline earth metal carbonate, preferably potassium carbonate, and/or the phase-transfer catalyst is tetrabutylammonium iodide.

The reaction is preferably performed in the presence of an organic solvent such as, for example, C$_1$-C$_4$ dialkyl ketones such as, for example, methyl ethyl ketone, acetone, or methyl isopropyl ketone, preferably methyl ethyl ketone.

In particular, the reaction is performed at a temperature of 50° C. to 80° C., preferably 55° C. to 65° C., preferably for 3 to 6 h. It is preferably performed with stirring.

The obtained compound of formula (II) can be isolated from the reaction medium by means of conventional techniques.

Method for Preparing Lemborexant

In a third aspect, the invention relates to a method for preparing Lemborexant which comprises:

a) performing the method defined in the second aspect in order to obtain the compound of formula (III) or a salt thereof

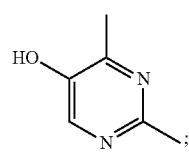
(III)

b) reacting the compound of formula (III) or a salt thereof with a compound of formula (VIII) in the presence of a base in order to yield a compound of formula (IX)

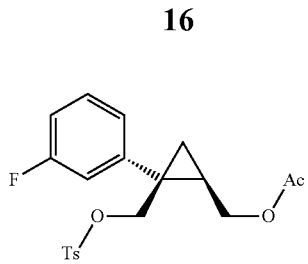
(VIII)

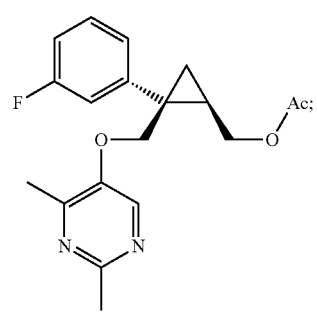
(IX)

c) hydrolyzing the compound of formula (IX) in the presence of a base in order to yield a compound of formula (X)

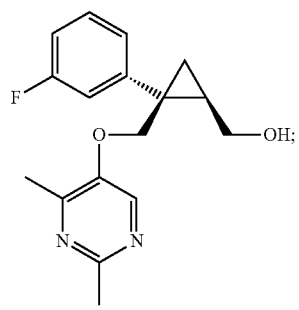
(X)

d) treating the compound of formula (X) with an oxidizing agent in order to yield a compound of formula (XI)

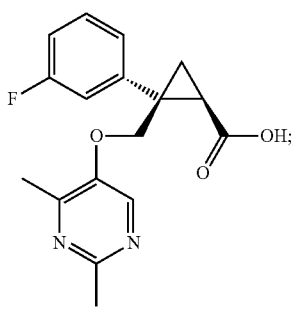
(XI)

and e) reacting the compound of formula (XI) with a compound of formula (XII) in the presence of a base and a coupling agent in order to yield Lemborexant

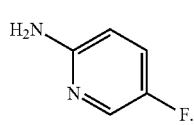

(XII)

The first step of the method of the third aspect is to carry out the method of the second aspect of the invention, described in detail above.

Step b) of the method of the third aspect comprises reacting the compound of formula (III) or a salt thereof with a compound of formula (VIII) in the presence of a base in order to yield a compound of formula (IX).

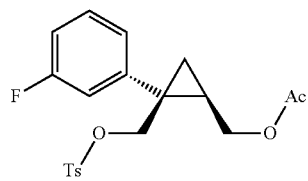

(VIII)

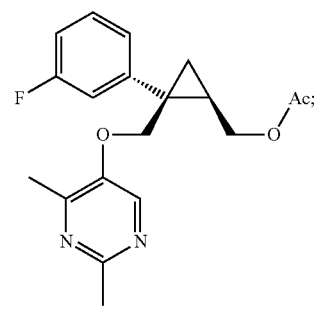

(IX)

The compound of formula (VIII) can be obtained following the synthetic method described in Example D of document EP2814798B1.

Bases suitable for the reaction of step b) are alkali metal carbonates, preferably cesium carbonate. In particular, 1 to 2 moles of base can be used for every mole of the compound of formula (VIII), preferably 1.5 to 2 moles. The reaction can be performed in the presence of an organic solvent such as, for example, acetonitrile, dichloromethane, tetrahydrofuran, 2-methyltetrahydrofuran, toluene, ethyl acetate, and a mixture thereof, preferably acetonitrile. The reaction can be carried out at a temperature of between 50° C. and 80° C., preferably between 65° C. and 75° C. In particular, step b) is carried out with stirring.

The compound of formula (IX) can be obtained with the specific conditions described in Example D of document EP2814798B1, which is incorporated herein by reference.

Step c) of the method of the third aspect comprises hydrolyzing the compound of formula (IX) in the presence of a base in order to yield a compound of formula (X).

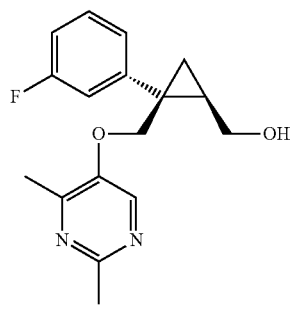

(X)

Bases suitable for said hydrolysis are alkali metal hydroxides, preferably sodium hydroxide. In particular, step c) is performed in the presence of water. In particular, step c) is performed at a temperature of 20° C. to 25° C. Preferably, step c) is performed with stirring.

The compound of formula (X) can be obtained with the specific conditions described in Example D of document EP2814798B1, which is incorporated herein by reference.

Step d) of the method of the third aspect comprises treating the compound of formula (X) with an oxidizing agent in order to yield a compound of formula (XI).

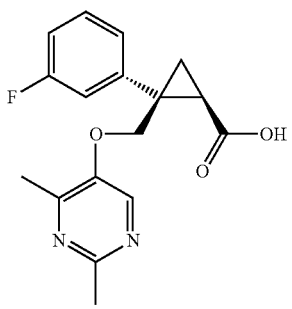

(XI)

The oxidizing agent of step d) is preferably NaClO and NaClO$_2$. Oxidation with NaClO oxidizes the alcohol group to aldehyde and oxidation with NaClO$_2$ oxidizes said aldehyde to an acid group, thereby yielding the compound of formula (XI). In particular, oxidation is performed in two steps, first with NaClO and, without isolating the aldehyde intermediate formed, oxidizing said aldehyde with NaClO$_2$ in the second step. In particular, 1 to 1.5 moles of oxidizing agent are used for every mole of the compound of formula (X). Preferably, 2,2,6,6-tetramethylpiperidine 1-oxyl (TEMPO) is furthermore used as a catalyst. In particular, the reaction is carried out in the presence of an aromatic hydrocarbon, preferably toluene. In particular, the reaction is carried out at a temperature of −5° C. to 5° C., preferably the addition of oxidizing agent/agents is carried out at a temperature of −5° C. to 5° C., and the reaction mixture is then kept at between 15° C. and 25° C. In particular, 1 to 1.5 moles of NaClO are used for every mole of the compound of formula (X), and in particular 1 to 1.2 moles of NaClO$_2$ are used for every mole of the compound of formula (X). Step d) is preferably performed with stirring.

The compound of formula (XI) can be obtained with the specific conditions described in Example F of document EP2814798B1, which is incorporated herein by reference.

Step e) of the method of the third aspect comprises reacting the compound of formula (XI) with a compound of formula (XII) in the presence of a base and a coupling agent in order to yield Lemborexant.

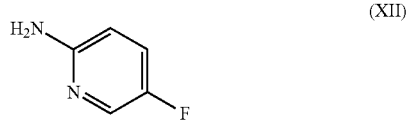

(XII)

Bases suitable for carrying out step e) are organic amines, preferably N(C$_1$-C$_4$ alkyl)$_3$ type amines in which each alkyl group is preferably independently selected from methyl, ethyl, and isopropyl. The organic amine is preferably N,N-diisopropylethylamine. In particular, 1 to 3 moles of base are used for every mole of the compound of formula (XI), preferably 1.8 to 2.2 moles.

An example of coupling agents suitable for step e) is propylphosphonic acid anhydride (T3P). In particular, 1 to 2 moles of coupling agent are used for every mole of the compound of formula (XI), preferably 1.2 to 1.6 moles.

In particular, step e) is performed in the presence of an organic solvent such as, for example, ethyl acetate, N,N-dimethylformamide, N,N-dimethylacetamide, N-methyl-2-pyrrolidone, acetone, toluene, acetonitrile, dichloromethane, and a mixture thereof, preferably ethyl acetate. Step e) is preferably performed with stirring.

Lemborexant can be obtained with the specific conditions described in Example G of document EP2814798B1, which is incorporated herein by reference.

Compound of Formula (IIa)

In a fourth aspect, the invention relates to a crystalline form of the compound of formula (IIa)

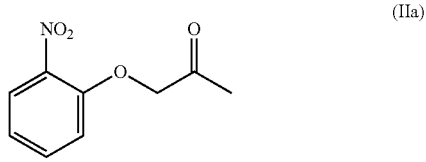

(IIa)

characterized in that it has an X-ray powder diffraction spectrum measured with CuKα radiation comprising peaks at 9.9, 12.2, 16.2, 18.7, 20.0, 24.5, 27.0 °2θ±0.2 °2θ.

In another embodiment, the crystalline form of the compound of formula (IIa) is characterized in that it has an X-ray powder diffraction spectrum measured with CuKα radiation essentially like the one shown in FIG. 1.

In another embodiment, the crystalline form of the compound of formula (IIa) is characterized in that it has a differential scanning calorimetry (DSC) diagram comprising an endothermic peak having a threshold temperature of about 57.6° C.±2° C. and an exothermic peak having a threshold temperature of about 208.0° C.±2° C.

Compound of Formula (Ia)

In a fifth aspect, the invention relates to a compound of formula (Ia) or a stereoisomer thereof

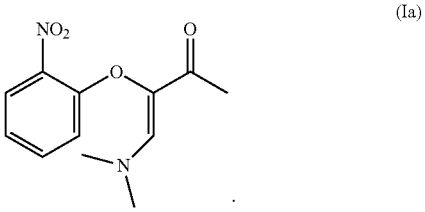 [SMILES: CC(=O)/C(=C/N(C)C)Oc1ccccc1[N+](=O)[O-]]

(Ia)

In a preferred embodiment, the compound of formula (Ia) is characterized in that it is a crystalline solid having an X-ray powder diffraction spectrum measured with CuKα radiation comprising peaks at 11.6, 16.6, 18.7, 21.5, 22.9, 23.4, 23.7, 26.4 °2θ±0.2 °2θ.

Figure 2:
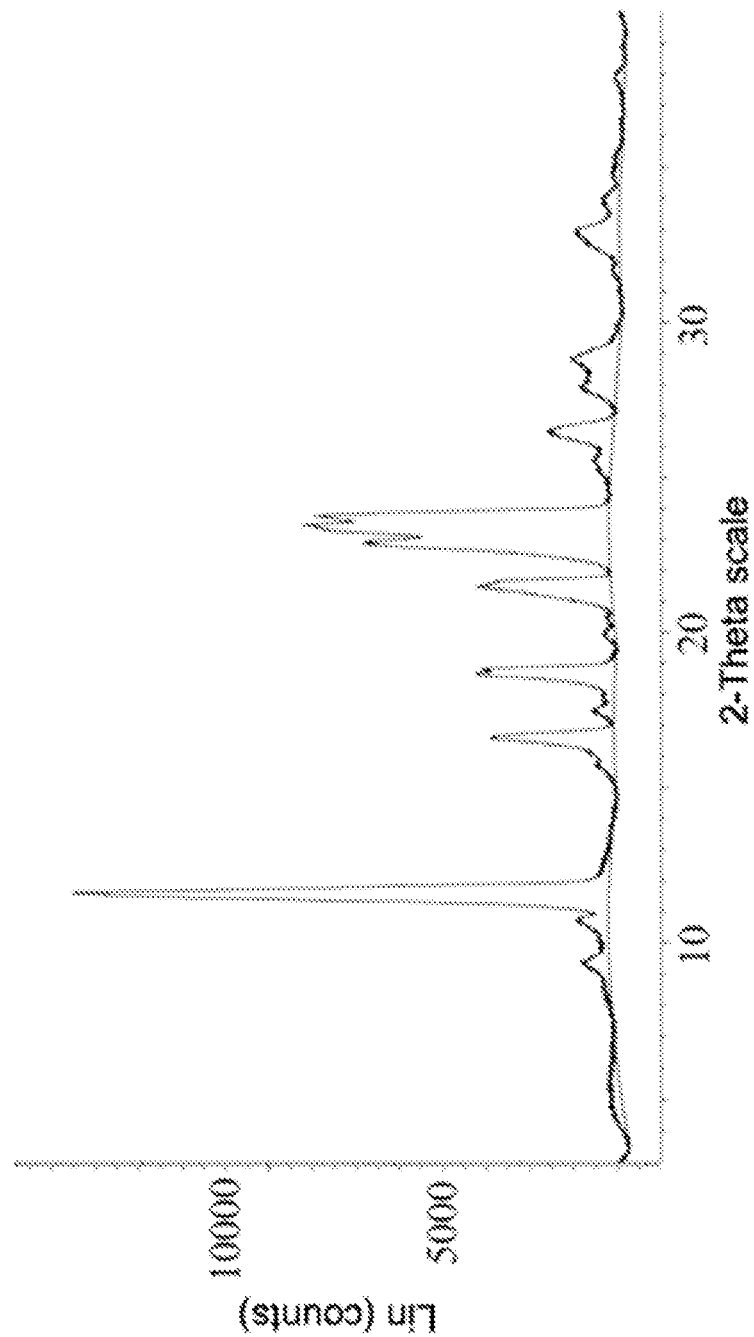
FIG. 2 shows the X-ray powder diffractogram (XRPD) of the compound of formula (Ia) corresponding to (Z)-4-(dimethylamino)-3-(2-nitrophenoxy)but-3-en-2-one.

In another embodiment, the compound of formula (Ia) is characterized in that it is a crystalline solid having an X-ray powder diffraction spectrum measured with CuKα radiation essentially like the one shown in FIG. 2.

In another embodiment, the compound of formula (Ia) is a crystalline solid as defined above which is furthermore characterized in that it has a differential scanning calorimetry (DSC) diagram comprising an endothermic peak having a threshold temperature of about 149.9° C.±2° C. and an exothermic peak having a threshold temperature of about 230.4° C.±2° C.

Stereoisomers of the compound of formula (Ia) refer to the position of the substituents with respect to the double bond, where they can be in a cis (Z) or trans (E) position.

The compound of formula (Ia) refers both to the cis isomer and to the trans isomer and any mixture thereof, preferably the cis isomer.

Compound of Formula (Va)

In a sixth aspect, the invention relates to a compound of formula (Va)

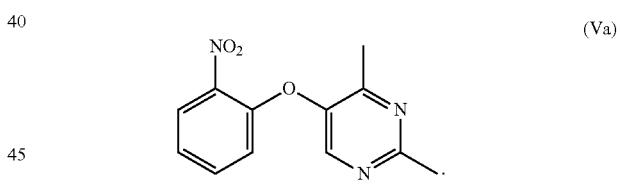

(Va)

In a preferred embodiment, the compound of formula (Va) is characterized in that it is a crystalline solid having an X-ray powder diffraction spectrum measured with CuKα radiation comprising peaks at 12.5, 14.6, 17.6, 23.6, 25.1 °2θ±0.2 °2θ.

Figure 3:
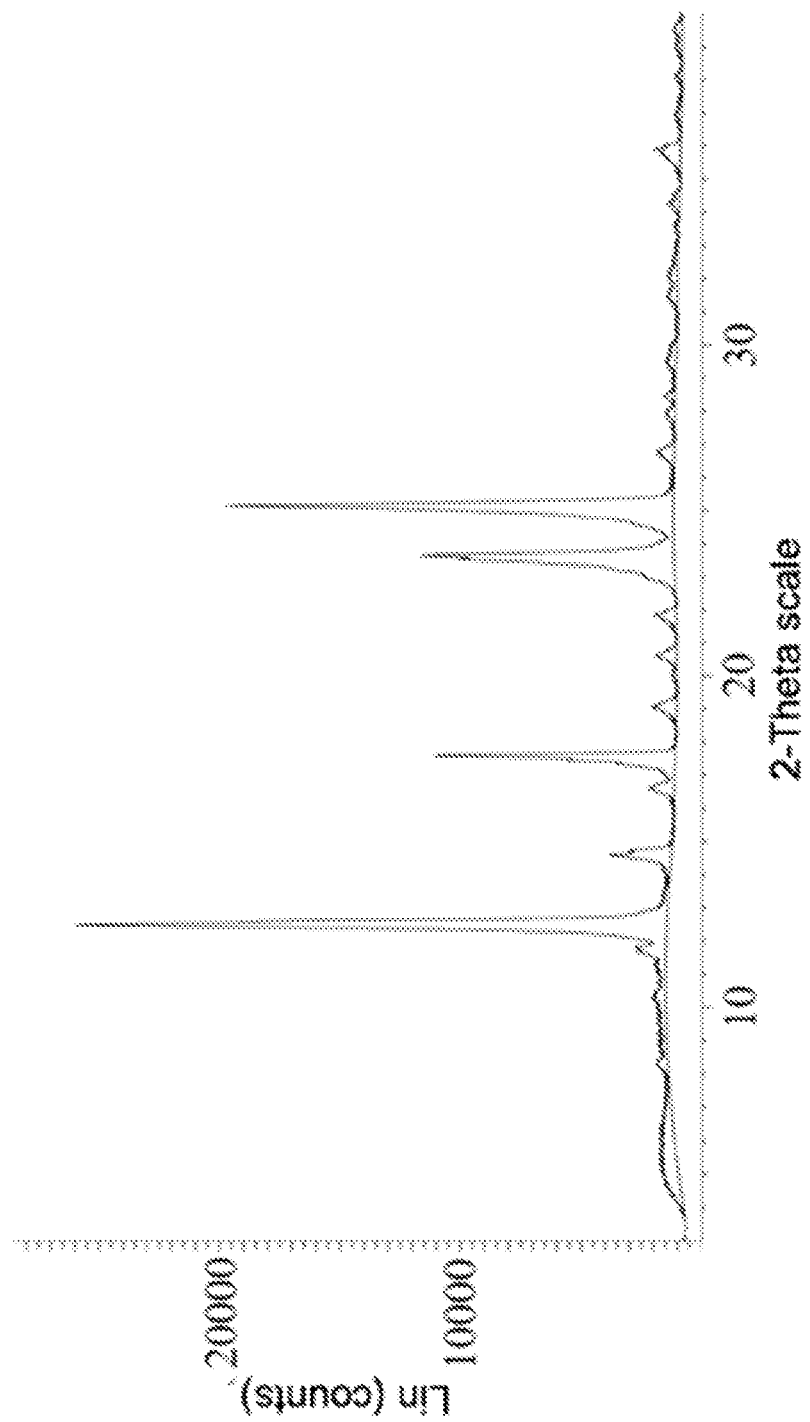
FIG. 3 shows the X-ray powder diffractogram (XRPD) of the compound of formula (Va) corresponding to 2,4-dimethyl-5-(2-nitrophenoxy)pyrimidine.

In another embodiment, the compound of formula (Va) is characterized in that it is a crystalline solid having an X-ray powder diffraction spectrum measured with CuKα radiation essentially like the one shown in FIG. 3.

In another embodiment, the compound of formula (Va) is a crystalline solid as defined above which is furthermore characterized in that it has a differential scanning calorimetry (DSC) diagram comprising an endothermic peak having a threshold temperature of about 104.9° C.±2° C.

Uses of the Compounds of Formula (IIa), (Ia), and (Va)

The compounds of formula (IIa), (Ia), and (Va), as well as their crystalline forms, described herein are novel intermediates of the method for the synthesis of the compound of formula (III) or a salt thereof and of Lemborexant.

Therefore, in another aspect, the invention relates to the use of the compound of formula (IIa), of the compound of formula (Ia) or a stereoisomer or salt thereof, of the compound of formula (Va), or of the crystalline forms of said compounds defined in the present invention in the preparation of the compound of formula (III) or a salt thereof.

(Va), and/or of the crystalline forms of said compounds defined in the present invention in the preparation of Lemborexant.

Lemborexant can be prepared from the key intermediate of formula (III) using the synthetic method described in EP3178814B1 and EP2814798B1 and the method defined in the third aspect of the present invention, which comprises the following steps:

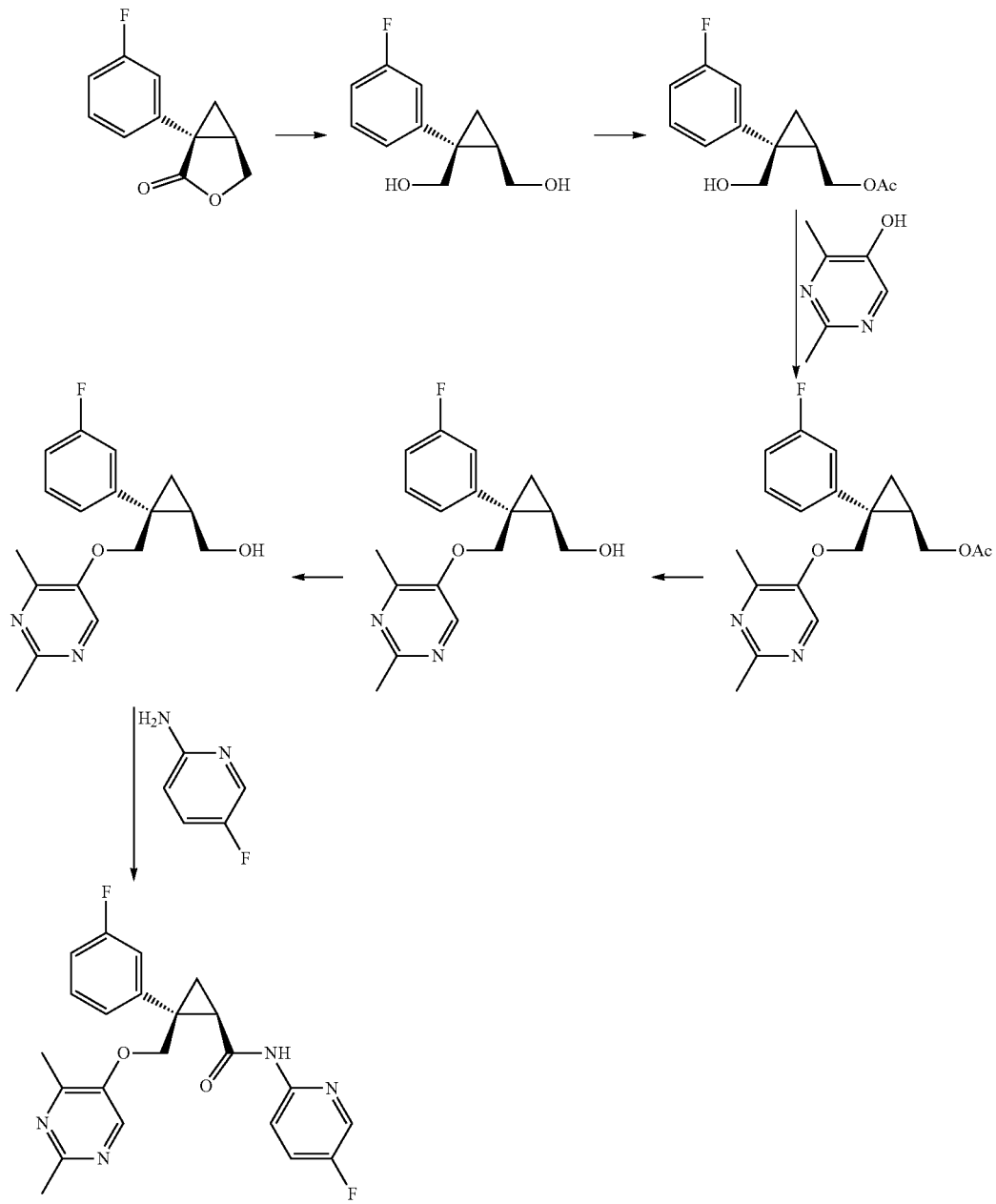

The compound of formula (III) or a salt thereof can be prepared using said intermediates, as described in detail in the first and second aspects of the present invention.

In another aspect, the invention relates to the use of the compound of formula (IIa), of the compound of formula (Ia) or a stereoisomer or salt thereof, of the compound of formula Polymorph of the Compound of Formula (III)

In another aspect, the invention relates to a crystalline form of the compound of formula (III) characterized in that the X-ray powder diffraction spectrum thereof measured with CuKα radiation comprises peaks at 12.8, 15.5, 16.6, 17.9, 21.8, 22.1, 23.6, 25.0, 25.7, 27.1, 30.1 °2θ±0.2 °2θ.

Figure 4:
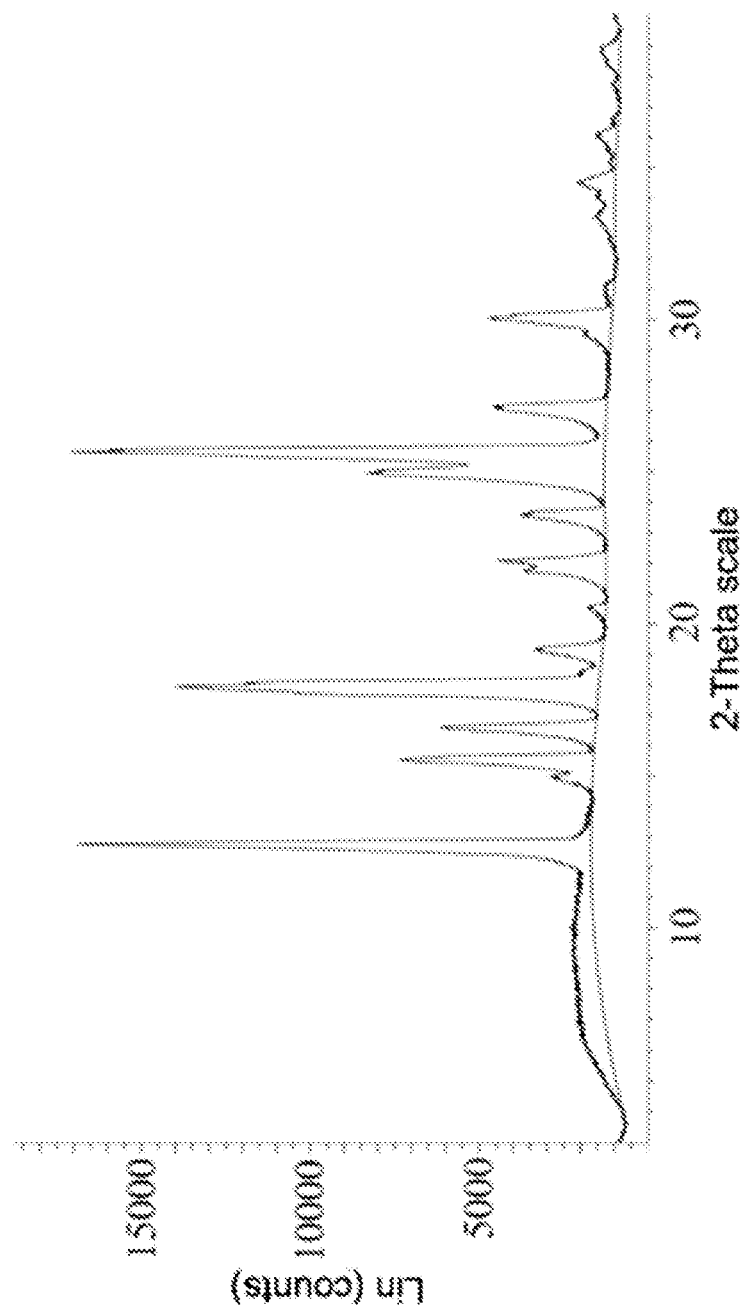
FIG. 4 shows the X-ray powder diffractogram (XRPD) of the compound of formula (III) corresponding to 2,4-dimethylpyrimidin-5-ol.

In another embodiment, the crystalline form of the compound of formula (III) is characterized in that it has an X-ray powder diffraction spectrum measured with CuKα radiation essentially like the one shown in FIG. 4.

In another embodiment, the crystalline form of the compound of formula (III) is characterized in that it has a differential scanning calorimetry (DSC) diagram comprising an endothermic peak having a threshold temperature of about 137.1° C.±2° C. and an endothermic peak having a threshold temperature of about 267.9° C.±2° C.

In the context of the present invention, X-ray diffractograms can be recorded using a powder diffraction system with a copper anode which emits CuKα radiation with a wavelength of 1.54 Å, in particular following the method described in the examples.

In the context of the present invention, differential scanning calorimetry diagrams can be obtained as described in the examples.

In the context of the present invention, threshold temperature or "T onset" refers to the temperature resulting from the extrapolation of the baseline before the start of transition and the baseline during energy absorption (tangent of the curve). It can be calculated as defined in standard DIN ISO 11357-1:2016(E).

In the context of the present invention, the terms "approximate" and "about" refer to the value which characterizes ±5% of said value.

In the context of the present invention, the term "base" refers to a substance capable of accepting a proton (of an acid).

Some examples of the experimental methods and embodiments of the present invention are described below to facilitate the understanding of the preceding ideas. Said examples are merely illustrative.

EXAMPLES

Example 1: Obtaining (Z)-4-(dimethylamino)-3-(4-nitrophenoxy)but-3-en-2-one 41.87 g (204.95 mmol) of 1-(4-nitrophenoxy)propan-2-one with a purity of 96.4% were mixed with 120 mL of toluene and 40.7 mL of N,N-dimethylformamide diethyl acetal (225.44 mmol). The obtained mixture was heated at the temperature of 80° C. to obtain a solution which was kept under stirring at the indicated temperature for 21 hours.

After being kept under stirring at said temperature, 80 mL of toluene were added, and the reaction mixture was cooled at the temperature of about 20° C. The reaction mass was then cooled at the temperature of 0-5° and kept under stirring for 1.5 hours. The resulting solid was filtered and dried in an oven at 25-30° C., finally obtaining 33.4 g of (Z)-4-(dimethylamino)-3-(4-nitrophenoxy)but-3-en-2-one (65.1% yield) with a purity of 99.9% by means of gas chromatography.

Example A1. Obtaining 1-(2-nitrophenoxy)propan-2-one 156.5 g (1.132 mol) of potassium carbonate were suspended in 900 mL of methyl ethyl ketone under nitrogen atmosphere at the temperature of about 20° C. While maintaining said temperature, 150.0 g (1.078 mol) of ortho-nitrophenol and 1 g of tetrabutylammonium iodide were slowly added. The obtained suspension was heated gradually at the temperature of 60-65° C. and a previously prepared solution of 94.14 mL (1.132 mol) of chloroacetone in 100 mL of methyl ethyl ketone was slowly added in said temperature interval. The reaction mixture was kept under stirring at the temperature of 60-65° C. for 4 hours.

After being kept under stirring at said temperature, the reaction mixture was cooled at the temperature of about 20° C., and the salts resulting from the reaction were filtered out. The solvent was vacuum-distilled to obtain 208.3 g of a solid corresponding to 1-(2-nitrophenoxy)propan-2-one (with a purity of 99.5% by means of gas chromatography).

The obtained product has a differential scanning calorimetry (DSC) diagram comprising an endothermic peak having a threshold temperature of about 57.6° C.±2° C. and an exothermic peak having a threshold temperature of about 208.0° C.±2° C.

$^1$H-NMR (d$_6$-DMSO, 400 MHz) δ (ppm): 7.92 (1H, dd), 7.63 (1H, t), 7.25 (1H, d), 7.16 (1H, t), 5.07 (2H, s), 2.21 (3H, s).

$^{13}$C-NMR (d$_6$-DMSO, 400 MHz) δ (ppm): 203.94, 151.41, 140.34, 135.05, 125.85, 121.84, 116.08, 73.71, 27.04.

FIG. 1 shows the X-ray powder diffractogram (XRPD, X-ray powder diffraction) obtained for 1-(2-nitrophenoxy)propan-2-one of Example A1. It has a crystalline form having peaks at the following angles (2θ)±0.2: 9.9, 12.2, 16.2, 18.7, 20.0, 24.5, 27.0.

Example A2. Obtaining (Z)-4-(dimethylamino)-3-(2-nitrophenoxy)but-3-en-2-one 30.16 g (153.76 mmol) of 1-(2-nitrophenoxy)propan-2-one obtained by means of Example A1 were mixed with 32.3 mL of N,N-dimethylformamide diethyl acetal (184.46 mmol), and the obtained mixture was heated at the temperature of 45-50° C. to obtain a solution which was kept under stirring at the indicated temperature for 4 hours.

After being kept under stirring at said temperature, 120 mL of diisopropyl ether were slowly added, maintaining the temperature of the mixture at 45-50° C. The obtained suspension was cooled at the temperature of 20° C. and kept under stirring for 12 hours. The mixture was then cooled at the temperature of 0-5° C., and the resulting solid was filtered and dried in an oven at 25-30° C., finally obtaining 33.3 g of (Z)-4-(dimethylamino)-3-(2-nitrophenoxy)but-3-en-2-one (85.2% yield from ortho-nitrophenol) with a purity of 99.6% by means of gas chromatography.

The obtained product has a differential scanning calorimetry (DSC) diagram comprising an endothermic peak having a threshold temperature of about 149.9° C.±2° C. and an exothermic peak having a threshold temperature of about 230.4° C.±2° C.

$^1$H-NMR (d$_6$-DMSO, 400 MHz) δ (ppm): 7.94 (d, 1H), 7.61 (d, 1H), 7.53 (s, 1H), 7.14 (t, 1H), 7.04 (s, 1H), 3.06 (s, 6H), 2.14 (s, 3H).

$^{13}$C-NMR (d$_6$-DMSO, 400 MHz) δ (ppm): 197.6, 152.52, 144.64, 139.69, 135.30, 134.20, 125.99, 125.41, 121.81, 117.04, 25.00.

FIG. 2 shows the X-ray powder diffractogram (XRPD, X-ray powder diffraction) obtained for (Z)-4-(dimethylamino)-3-(2-nitrophenoxy)but-3-en-2-one of Example A2. It has a crystalline form having peaks at the following angles (2θ)±0.2: 11.6, 16.6, 18.7, 21.5, 22.9, 23.4, 23.7, 26.4.

Example A3. Obtaining 2,4-dimethyl-5-(2-nitrophenoxy)pyrimidine 49.3 g (695.6 mmols) of 96% EtONa were slowly added to 362 mL of ethanol, maintaining the temperature at 15-20°

C. 67.1 g (695.6 mmol) of 98% acetamidine hydrochloride were slowly added to the resulting solution at the temperature of 25-30° C. While maintaining said temperature, 72.5 g (289.7 mmol) of (Z)-4-(dimethylamino)-3-(2-nitrophenoxy)but-3-en-2-one were slowly added. The reaction mixture was heated to the temperature of 75-80° C. and kept under stirring at said temperature for 4 hours.

After being kept under stirring at said temperature, the reaction mixture was cooled at 18-20° C., kept under stirring at said temperature for 1 hour, and the resulting solid was filtered. The solvent was vacuum-distilled from the solution thereby obtained in order to yield a solid corresponding to 2,4-dimethyl-5-(2-nitrophenoxy)pyrimidine.

The obtained product has a differential scanning calorimetry (DSC) diagram comprising an endothermic peak having a threshold temperature of about 104.9° C.±2° C.

$^1$H-NMR (d$_6$-DMSO, 400 MHz) δ (ppm): 8.40 (s, 1H), 8.14 (dd, 1H), 7.71 (m, 1H), 7.42 (m, 1H), 7.16 (dd, 1H), 2.64 (s, 3H), 2.40 (s, 3H).

$^{13}$C-NMR (d$_6$-DMSO, 400 MHz) δ (ppm): 164.12, 159.43, 149.70, 148.30, 147.40, 141.16, 136.15, 126.80, 125.24, 119.99, 25.79, 19.32.

FIG. 3 shows the X-ray powder diffractogram (XRPD, X-ray powder diffraction) obtained for 2,4-dimethyl-5-(2-nitrophenoxy)pyrimidine of Example A3. It has a crystalline form having peaks at the following angles (2θ)±0.2: 12.5, 14.6, 17.6, 23.6, 25.1.

Example A4. Obtaining 2,4-dimethylpyrimidin-5-ol

The solid obtained in the step of Example A3 was dissolved in 350 mL of methanol at the temperature of about 20° C. While maintaining the temperature between 35 and 40° C., 72.4 g (869.1 mmol) of a previously prepared 48 wt % aqueous sodium hydroxide solution were slowly added. The reaction mixture was heated at the temperature of about 65° C. and kept under stirring at said temperature for 20 hours.

After being kept under stirring at said temperature, the reaction mixture was cooled at 30-35° C., and a solvent of about 150 mL in volume was vacuum-distilled. 325 mL of water and 70 mL of toluene were added, and the resulting mixture was kept under stirring for 1 hour at the temperature of 30-35° C. The resulting organic phase was separated, and 60 mL of toluene were added to the aqueous phase maintaining the mentioned temperature. The new organic phase was separated, and the resulting aqueous phase was cooled at the temperature of about 20° C. A 36% aqueous HCl solution was slowly added until a pH value of about 3.5. The aqueous solution thereby obtained was washed with two consecutive fractions of 60 mL of toluene each, and pH was then adjusted with a 30% aqueous NaOH solution to the value of about 5.5. 2 g of carbon and 2 g of diatomaceous earth were added, and the resulting mixture was kept under stirring at the temperature of 35-40° C. for 30 minutes. Solids were separated by means of filtration and washed with three fractions of 20 mL of water which were pooled with the previously obtained aqueous solution. pH was adjusted with a 30% aqueous NaOH solution until a value of 6-7, and 150 mL of ethyl acetate were added. The organic phase was separated, and the aqueous phase was washed with two additional fractions of 150 mL of ethyl acetate each. The solvent was vacuum-distilled from the pooled organic phases to obtain 32.0 g (257.8 mmol) of a solid corresponding to 2,4-dimethylpyrimidin-5-ol (88.9% yield from (Z)-4-(dimethylamino)-3-(2-nitrophenoxy)but-3-en-2-one) with a purity of 99.6% by means of gas chromatography analysis or 99.78% by means of UHPLC analysis.

The obtained product has a differential scanning calorimetry (DSC) diagram comprising two endothermic peaks having a threshold temperature of about 137.1° C.±2° C. and 267.9° C.±2° C.

FIG. 4 shows the X-ray powder diffractogram (XRPD, X-ray powder diffraction) obtained for 2,4-dimethylpyrimidin-5-ol of Example A4. It has a crystalline form having peaks at the following angles (2θ)±0.2: 12.8, 15.5, 16.6, 17.9, 21.8, 22.1, 23.6, 25.0, 25.7, 27.1, 30.1.

Example B1. Obtaining 1-(4-nitrophenoxy)propan-2-one 52.16 g (377.4 mmol) of potassium carbonate were suspended in 175 mL of methyl ethyl ketone under nitrogen atmosphere at the temperature of about 20° C. While maintaining said temperature, 50.0 g (359.4 mmol) of para-nitrophenol and 0.25 g of tetrabutylammonium iodide were slowly added. The obtained suspension was heated gradually at the temperature of 55-60° C., and 31.4 mL of chloroacetone were slowly added in said temperature interval. The reaction mixture was heated at the temperature of 65-70° C. and kept under stirring at said temperature for 4 hours.

After being kept under stirring at said temperature, the reaction mixture was cooled at the temperature of about 20° C., and the salts resulting from the reaction were filtered. The solvent was vacuum-distilled to obtain 73.5 g of a solid corresponding to 1-(4-nitrophenoxy)propan-2-one.

Example B2. Obtaining (Z)-4-(dimethylamino)-3-(4-nitrophenoxy)but-3-en-2-one 31.4 g (153.7 mmol) of 1-(4-nitrophenoxy)propan-2-one obtained by means of Example B1 were mixed with 33.3 mL of N,N-dimethylformamide diethyl acetal (184.45 mmol), and the obtained mixture was heated at the temperature of 45-50° C. to obtain a solution which was kept under stirring at the indicated temperature for 4 hours.

After being kept under stirring at said temperature, 120 mL of diisopropyl ether were slowly added, maintaining the temperature of the mixture at 45-50° C. The obtained suspension was cooled at the temperature of 20° C. and kept under stirring for 12 hours. The mixture was then cooled at the temperature of 0-5° C. and kept under stirring for 1 hour. The resulting solid was filtered and dried in an oven at 25-30° C., finally obtaining 26.36 g of (Z)-4-(dimethylamino)-3-(4-nitrophenoxy)but-3-en-2-one (68.6% yield from para-nitrophenol) with a purity of 99.5% by means of gas chromatography.

Example B3. Obtaining 2,4-dimethyl-5-(4-nitrophenoxy)pyrimidine 24.4 g (252.8 mmol) of 98% acetamidine hydrochloride were mixed with 260 mL of methanol.

While maintaining the temperature between 20 and 30° C., 45.5 g of a previously prepared 30 wt % solution of sodium methoxide in methanol were slowly added, and 26.36 g (105.3 mmol) of (Z)-4-(dimethylamino)-3-(4-nitrophenoxy)but-3-en-2-one were then slowly added. The reaction mixture was heated to the temperature of 65-70° C. and kept under stirring at said temperature for 6 hours.

After being kept under stirring at said temperature, the reaction mixture was cooled at 18-20° C., kept under stirring at said temperature for 1 hour, and the resulting solid was filtered. The solvent was vacuum-distilled from the solution thereby obtained in order to yield a solid corresponding to 2,4-dimethyl-5-(4-nitrophenoxy)pyrimidine.

Example B4. Obtaining 2,4-dimethylpyrimidin-5-ol

The solid obtained in the step of Example B3 was dissolved in 130 mL of methanol at the temperature of about 20° C. While maintaining the temperature between 35 and 40° C., 26.4 g (316.0 mmol) of a previously prepared 48 wt % aqueous sodium hydroxide solution were slowly added. The reaction mixture was heated at the temperature of about 65° C. and kept under stirring at said temperature for 12 hours.

After being kept under stirring at said temperature, the reaction mixture was cooled at 30-35° C., and a solvent of about 65 mL in volume was vacuum-distilled. 130 mL of water and 40 mL of toluene were added, and the resulting mixture was kept under stirring for 1 hour at the temperature of 30-35° C. The resulting organic phase was separated, and 40 mL of toluene were added to the aqueous phase maintaining the mentioned temperature. The new organic phase was separated, and the resulting aqueous phase was cooled at the temperature of about 20° C. A 36% aqueous HCl solution was slowly added until a pH value of about 3.5 was reached. The aqueous solution thereby obtained was washed with two consecutive fractions of 40 mL of toluene each and pH was then adjusted with a 30% aqueous NaOH solution to the value of about 5.5. 1.5 g of carbon and 1.5 g of diatomaceous earth were added, and the resulting mixture was kept under stirring at the temperature of 20-25° C. for 30 minutes. Solids were separated by means of filtration and washed with three fractions of 10 mL of water which were pooled with the previously obtained aqueous solution. pH was adjusted with a 30% aqueous NaOH solution until a value of 6-7 and 100 mL of ethyl acetate were added. The organic phase was separated, and the aqueous phase was washed with two additional fractions of 80 mL of ethyl acetate each. The solvent was vacuum-distilled from the pooled organic phases to obtain 10.43 g of a solid corresponding to 2,4-dimethylpyrimidin-5-ol (79.7% yield from (Z)-4-(dimethylamino)-3-(4-nitrophenoxy)but-3-en-2-one) with a purity of 99.7% by means of gas chromatography analysis or 99.81% by means of UHPLC analysis.

Materials and Methods

Chromatography

In those cases in which the purity of the products obtained was analyzed by means of gas chromatography, the following experimental conditions were followed:
Non-polar CP Sil 5CB column (open tubular fused silica column measuring 10 m×0.53 mm)
Injector temperature: 220° C.
Detector temperature: 260° C.
Column temperature: 10° C./min gradient from 50 to 250° C., maintaining at 250° C. for 10 min
Sensitivity: $10^{-10}$
Attenuation: 4
Carrier gas: $N_2$
Injector: split (split sample injection)
In those cases in which the purity of the products obtained was analyzed by means of ultra-high performance liquid chromatography (UHPLC), a Waters apparatus equipped with a variable wavelength detector and a thermostatic oven for the column was used. A CSH C18 column (1.7 μm×50 mm and 3 mm) and mobile phases A (ammonium acetate 10 mM, pH 4.8) and B (acetonitrile) with the following conditions of analysis were used:
Flow rate: (mL/min): 0.5
Column temperature (° C.): 40
Wavelength (nm): 225
Injection volume (μL): 1
Acquisition time (min): 10
Diluent: acetonitrile/water (1:1)
Gradient:

| t (min) | % of A | % of B |
|---|---|---|
| 0 | 95 | 5 |
| 0.5 | 95 | 5 |
| 4.5 | 30 | 70 |
| 5.5 | 30 | 70 |
| 6.5 | 5 | 95 |
| 8 | 5 | 95 |
| 9.5 | 95 | 5 |
| 10 | 95 | 5 |

Differential Scanning Calorimetry (DSC)

DSC analysis was performed in a Mettler Toledo 822e apparatus with STARe SW15 software. Parameters: heating range of 30 to 300° C. with a 10° C./min ramp and $N_2$ flow of 50 mL/min. The measurement is taken with a closed perforated capsule.

Nuclear Magnetic Resonance

Proton nuclear magnetic resonance analysis ($^1$H-NMR) and $^{13}$C-NMR were performed in a 400 MHz Brucker Avance III spectrometer. Chemical shifts are in reference to the DMSO-$d_6$ signal (2.54 ppm for proton and 40.5 ppm for carbon).

X-Ray Crystallography (XRPD)

XRPD analysis was performed using a BRUKER D2 PHASER X-ray powder diffractometer equipped with a copper anode. The radiation used is CuKα with a wavelength of 1.54060 Å. Scan parameters: 3-50 2θ degrees, continuous scan, ratio: 5.6 degrees/minute.

As herein above described the present invention encompasses the following aspects and embodiments:

Embodiment 1. A method for preparing a compound of formula (I) or a stereoisomer or salt thereof

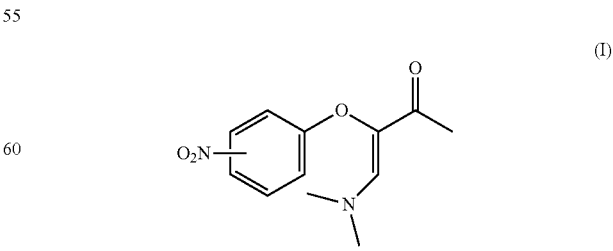

which comprises reacting a compound of formula (II) with N,N-dimethylformamide diethyl acetal

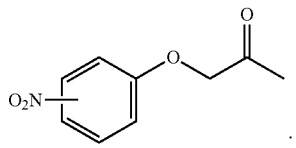 (II)

Embodiment 2. The method according to Embodiment 1, wherein the —NO₂ group of the compounds of formula (I) and formula (II) is in an ortho or para position, preferably an ortho position.

Embodiment 3. The method according to any of the preceding Embodiments, wherein the proportion of N,N-dimethylformamide diethyl acetal with respect to the compound of formula (II) is from 1 to 2 moles of N,N-dimethylformamide diethyl acetal for every mole of the compound of formula (II).

Embodiment 4. The method according to any of the preceding Embodiments, wherein the method is carried out in the presence of toluene.

Embodiment 5. The method according to any of Embodiment 1 to 3, wherein the method is carried out in the absence of solvent.

Embodiment 6. The method according to any of the preceding Embodiments, wherein the method is carried out at a temperature of between 45 and 50° C.

Embodiment 7. The method according to any of the preceding Embodiments, comprising a later step of treatment with diisopropyl ether, preferably from 3 to 5 mL of diisopropyl ether for every gram of compound of formula (II).

Embodiment 8. The method according to Embodiment 7, wherein treatment with diisopropyl ether is performed at a temperature of 20 to 25° C.

Embodiment 9. A method for preparing the compound of formula (III) or a salt thereof

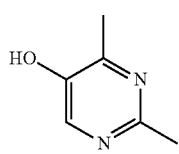 (III)

which comprises:
performing the method defined in any of the preceding Embodiments in order to obtain the compound of formula (I) or a stereoisomer or salt thereof

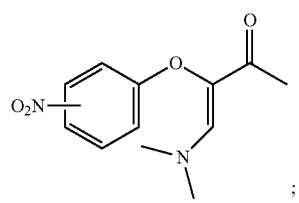 (I)

and transforming the compound of formula (I) or a stereoisomer or salt thereof into a compound of formula (III) or a salt thereof.

Embodiment 10. The method according to Embodiment 9, which comprises:
a) performing the method defined in any of the preceding Embodiments in order to obtain the compound of formula (I) or a stereoisomer or salt thereof

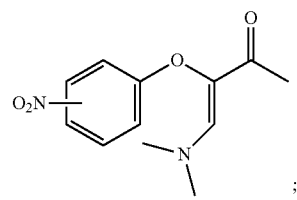 (I)

b) reacting the compound of formula (I) or a stereoisomer or salt thereof with the compound of formula (IV) or a salt thereof in the presence of a base in order to yield the compound of formula (V) or a salt thereof

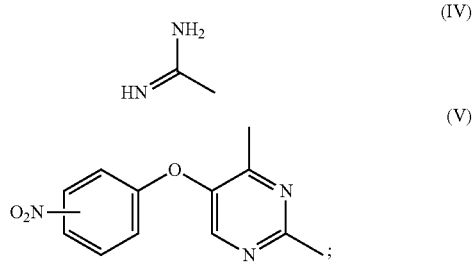

(IV)

(V)

and
c) hydrolyzing the compound of formula (V) or a salt thereof in order to yield the compound of formula (III) or a salt thereof.

Embodiment 11. The method according to Embodiments 9 or 10, wherein the —NO₂ group of the compound of formula (I) and of the compound of formula (V) is in an ortho or para position, preferably an ortho position.

Embodiment 12. The method according to Embodiments 10 or 11, wherein the base of step b) is an alkali metal $C_1$-$C_4$ alkoxide, preferably a sodium $C_1$-$C_4$ alkoxide, more preferably sodium ethoxide or sodium methoxide, even more preferably sodium ethoxide.

Embodiment 13. The method according to any of Embodiments 10 to 12, wherein step b) is performed in the presence of a solvent selected from the group consisting of $C_1$-$C_4$ alkanol, preferably ethanol, methanol, or a mixture thereof, even more preferably ethanol.

Embodiment 14. The method according to any of Embodiments 10 to 13, wherein step c) is performed in the presence of a base selected from the group consisting of alkali metal hydroxide, alkali metal carbonate, and alkaline earth metal carbonate.

Embodiment 15. The method according to Embodiment 14, wherein the base is selected from the group consisting of sodium hydroxide and potassium carbonate, preferably sodium hydroxide.

Embodiment 16. The method according to any of Embodiments 10 to 15, wherein step c) is performed in the presence of an aqueous solvent, preferably a mixture of water and $C_1$-$C_4$ alkanol, preferably a mixture of water and ethanol or a mixture of water and methanol, even more preferably a mixture of water and ethanol.

Embodiment 17. The method according to any of Embodiments 1 to 16, wherein the compound of formula (II) is obtained by means of the reaction of a compound of formula (VI) and a compound of formula (VII), wherein X is chlorine or bromine, preferably chlorine.

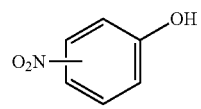
(VI)

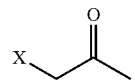
(VII)

Embodiment 18. The method according to Embodiment 17, wherein the —NO$_2$ group of the compound of formula (VI) is in an ortho or para position, preferably an ortho position.

Embodiment 19. The method according to Embodiments 17 or 18, wherein the reaction is carried out in the presence of a base and a phase-transfer catalyst.

Embodiment 20. The method according to Embodiment 19, wherein the base is an alkali metal or alkaline earth metal carbonate, preferably potassium carbonate, and/or the phase-transfer catalyst is tetrabutylammonium iodide.

Embodiment 21. A method for preparing Lemborexant which comprises:

a) performing the method defined in any of Embodiments 9 to 20 in order to obtain the compound of formula (III) or a salt thereof

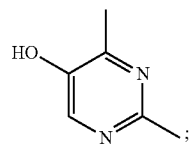
(III)

b) reacting the compound of formula (III) or a salt thereof with a compound of formula (VIII) in the presence of a base in order to yield a compound of formula (IX)

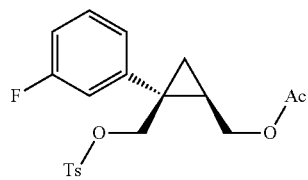
(VIII)

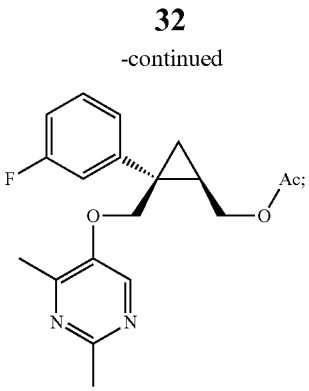
(IX)

c) hydrolyzing the compound of formula (IX) in the presence of a base in order to yield a compound of formula (X)

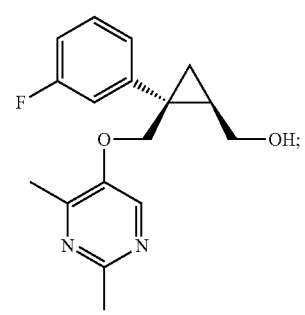
(X)

d) treating the compound of formula (X) with an oxidizing agent in order to yield a compound of formula (XI)

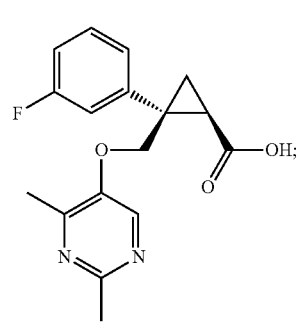
(XI)

and e) reacting the compound of formula (XI) with a compound of formula (XII) in the presence of a base and a coupling agent in order to yield Lemborexant

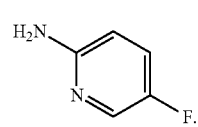
(XII)

Embodiment 22. The method according to Embodiment 21, wherein the base of step b) is an alkali metal carbonate, preferably cesium carbonate.

Embodiment 23. The method according to any of Embodiments 21 or 22, wherein the base of step c) is sodium hydroxide.

Embodiment 24. The method according to any of Embodiments 21 to 23, wherein the oxidizing agent of step d) is NaClO and NaClO$_2$.

Embodiment 25. The method according to any of Embodiments 21 to 24, wherein the base of step e) is an organic amine, preferably N,N-diisopropylethylamine, and/or the coupling agent of step e) is propylphosphonic acid anhydride.

Embodiment 26. A crystalline form of the compound of formula (IIa)

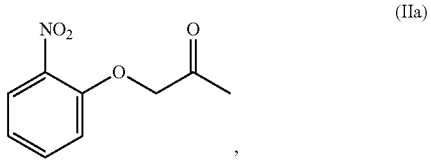

(IIa)

characterized in that it has an X-ray powder diffraction spectrum measured with CuKα radiation comprising peaks at 9.9, 12.2, 16.2, 18.7, 20.0, 24.5, 27.0 °2θ±0.2 °2θ.

Embodiment 27. The crystalline form of the compound of formula (IIa) according to Embodiment 26, characterized in that it has a differential scanning calorimetry (DSC) diagram comprising an endothermic peak having a threshold temperature of about 57.6° C.±2° C. and an exothermic peak having a threshold temperature of about 208.0° C.±2° C.

Embodiment 28. A compound of formula (Ia) or a stereoisomer or salt thereof

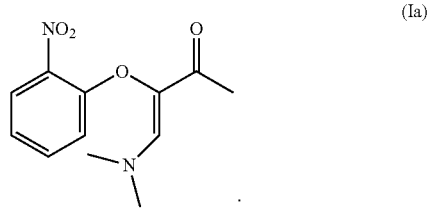 [SMILES: CC(=O)/C(=C/N(C)C)Oc1ccccc1[N+](=O)[O-]]

(Ia)

Embodiment 29. The compound of formula (Ia) according to Embodiment 28, characterized in that it is a crystalline solid having an X-ray powder diffraction spectrum measured with CuKα radiation comprising peaks at 11.6, 16.6, 18.7, 21.5, 22.9, 23.4, 23.7, 26.4 °2θ±0.2 °θ.

Embodiment 30. The compound of formula (Ia) according to Embodiment 29, characterized in that it has a differential scanning calorimetry (DSC) diagram comprising an endothermic peak having a threshold temperature of about 149.9° C.±2° C. and an exothermic peak having a threshold temperature of about 230.4° C.±2° C.

Embodiment 31. A compound of formula (Va)

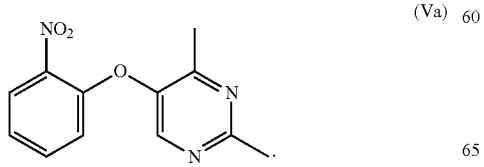

(Va)

Embodiment 32. The compound of formula (Va) according to Embodiment 31, characterized in that it is a crystalline solid having an X-ray powder diffraction spectrum measured with CuKα radiation comprising peaks at 12.5, 14.6, 17.6, 23.6, 25.1 °2θ±0.2 °2θ.

Embodiment 33. The compound of formula (Va) according to Embodiment 32, characterized in that it has a differential scanning calorimetry (DSC) diagram comprising an endothermic peak having a threshold temperature of about 104.9° C.±2° C.

Embodiment 34. Use of a compound of formula (IIa), of the crystalline form of the compound of formula (IIa) according to any of Embodiments 26 or 27, of the compound of formula (Ia) or a stereoisomer thereof according to any of Embodiments 28 to 30, and/or of the compound of formula (Va) according to any of Embodiments 31 to 33 in the preparation of the compound of formula (III) or a salt thereof.

Embodiment 35. Use of a compound of formula (IIa), of the crystalline form of the compound of formula (IIa) according to any of Embodiments 26 or 27, of the compound of formula (Ia) or a stereoisomer thereof according to any of Embodiments 28 to 30, and/or of the compound of formula (Va) according to any of Embodiments 31 to 33 in the preparation of Lemborexant.

Embodiment 36. A crystalline form of the compound of formula (III), characterized in that the X-ray powder diffraction spectrum thereof measured with CuKα radiation comprises peaks at 12.8, 15.5, 16.6, 17.9, 21.8, 22.1, 23.6, 25.0, 25.7, 27.1, 30.1 °2θ±0.2 °2θ.

Embodiment 37. The crystalline form according to Embodiment 36, characterized in that it has a differential scanning calorimetry (DSC) diagram comprising an endothermic peak having a threshold temperature of about 137.1° C.±2° C. and an endothermic peak having a threshold temperature of about 267.9° C.±2° C.

What is claimed is:

1. A method for preparing a compound of formula (I) or a stereoisomer or salt thereof

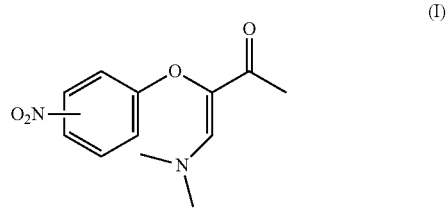

(I)

which comprises reacting a compound of formula (II) with N,N-dimethylformamide diethyl acetal

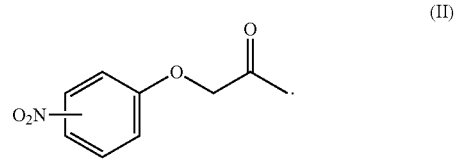

(II)

2. The method according to claim 1, wherein the —NO$_2$ group of the compounds of formula (I) and formula (II) is in an ortho or para position.

3. The method according to claim 1, wherein the proportion of N,N-dimethylformamide diethyl acetal with respect to the compound of formula (II) is from 1 to 2 moles of N,N-dimethylformamide diethyl acetal for every mole of the compound of formula (II).

4. The method according to claim 1, wherein the method is carried out in the absence of solvent.

5. A method for preparing a compound of formula (III) or a salt thereof, which comprises:

a) performing the method of claim 1 in order to obtain the compound of formula (I) or a stereoisomer or salt thereof

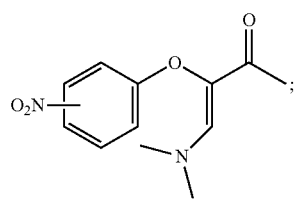
(I)

b) reacting the compound of formula (I) or a stereoisomer or salt thereof with a compound of formula (IV) or a salt thereof in the presence of a base in order to yield a compound of formula (V) or a salt thereof

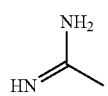
(IV)

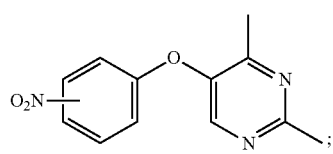
(V)

and c) hydrolyzing the compound of formula (V) or a salt thereof in order to yield the compound of formula (III) or a salt thereof

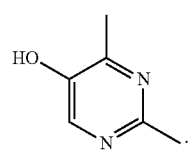
(III)

6. The method according to claim 5, wherein the —NO$_2$ group of the compound of formula (I) and of the compound of formula (V) is in an ortho or para position.

7. The method according to claim 5, wherein the base of said b) is an alkali metal $C_1$-$C_4$ alkoxide.

8. The method according to claim 5, wherein said c) is performed in the presence of an aqueous solvent.

9. The method according to claim 1, wherein the compound of formula (II) is obtained by means of the reaction of a compound of formula (VI) and a compound of formula (VII), wherein X is chlorine or bromine.

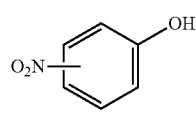
(VI)

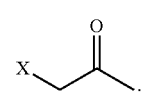
(VII)

10. The method according to claim 9, wherein the —NO$_2$ group of the compound of formula (VI) is in an ortho or para position.

11. A method for preparing Lemborexant which comprises:

a) performing the method of claim 5, to obtain the compound of formula (III) or a salt thereof

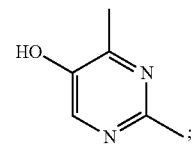
(III)

b) reacting the compound of formula (III) or a salt thereof with a compound of formula (VIII) in the presence of a base in order to yield a compound of formula (IX)

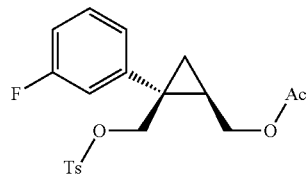
(VIII)

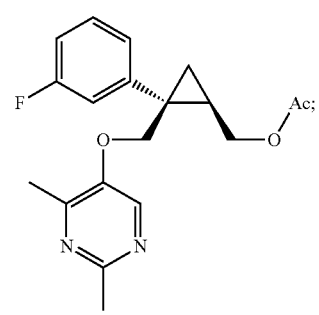
(IX)

c) hydrolyzing the compound of formula (IX) in the presence of a base in order to yield a compound of formula (X)

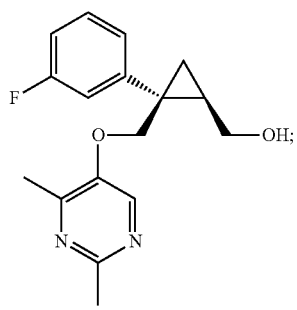

d) treating the compound of formula (X) with an oxidizing agent in order to yield a compound of formula (XI)

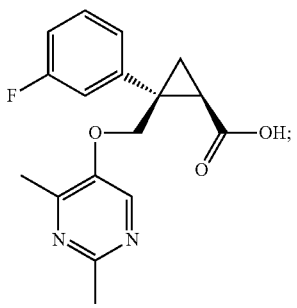

and e) reacting the compound of formula (XI) with a compound of formula (XII) in the presence of a base and a coupling agent in order to yield Lemborexant

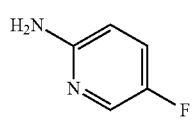

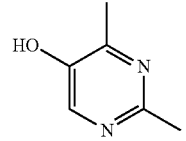

Lemborexant

12. The method according to claim 11, wherein the base of said b) is an alkali metal carbonate.

13. The method according to claim 11, wherein the base of said c) is sodium hydroxide.

14. The method according to claim 11, wherein the oxidizing agent of said d) is NaClO and NaClO$_2$.

15. The method according to claim 11, wherein the base of said e) is an organic amine, and/or the coupling agent of step e) is propylphosphonic acid anhydride.

16. A crystalline form of a compound of formula (III)

(III)

characterized in that the X-ray powder diffraction spectrum thereof measured with CuKα radiation comprises peaks at 12.8, 15.5, 16.6, 17.9, 21.8, 22.1, 23.6, 25.0, 25.7, 27.1, 30.1 °2θ±0.2 °2θ.

17. The method according to claim 1, wherein the —NO$_2$ group of the compounds of formula (I) and formula (II) is in an ortho position.

18. The method according to claim 5, wherein the —NO$_2$ group of the compound of formula (I) and of the compound of formula (V) is in an ortho position.

19. The method according to claim 9, wherein the —NO$_2$ group of the compound of formula (VI) is in an ortho position.

\* \* \* \* \*